United States Patent
Berlinger

(10) Patent No.: US 11,443,441 B2
(45) Date of Patent: Sep. 13, 2022

(54) DEEP INSPIRATION BREATH-HOLD SETUP USING X-RAY IMAGING

(71) Applicant: Brainlab AG, Munich (DE)

(72) Inventor: Kajetan Berlinger, Munich (DE)

(73) Assignee: Brainlab AG, Munich (DE)

( * ) Notice: Subject to any disclaimer, the term of this patent is extended or adjusted under 35 U.S.C. 154(b) by 650 days.

(21) Appl. No.: 16/476,941

(22) PCT Filed: Feb. 24, 2017

(86) PCT No.: PCT/EP2017/054323
§ 371 (c)(1),
(2) Date: Jul. 10, 2019

(87) PCT Pub. No.: WO2018/153473
PCT Pub. Date: Aug. 30, 2018

(65) Prior Publication Data
US 2019/0366124 A1 Dec. 5, 2019

(51) Int. Cl.
*A61N 5/00* (2006.01)
*G06T 7/33* (2017.01)
(Continued)

(52) U.S. Cl.
CPC .............. *G06T 7/33* (2017.01); *A61B 5/0077* (2013.01); *A61B 5/7292* (2013.01); *A61B 34/10* (2016.02);
(Continued)

(58) Field of Classification Search
CPC ......... G06T 7/33; G06T 7/0014; G06T 7/248; G06T 7/251; G06T 7/30; G06T 7/74;
(Continued)

(56) References Cited

U.S. PATENT DOCUMENTS

| | | | |
|---|---|---|---|
| 6,580,938 B1 * | 6/2003 | Acker | A61B 5/062 600/429 |
| 6,621,889 B1 * | 9/2003 | Mostafavi | A61N 5/1048 378/65 |

(Continued)

FOREIGN PATENT DOCUMENTS

| | | | | |
|---|---|---|---|---|
| AU | 2004203173 A1 * | 2/2005 | | A61B 19/52 |
| JP | 4342644 B2 * | 10/2009 | | |

(Continued)

OTHER PUBLICATIONS

Borst et al., "Clinical Results of Image-Guided Deep Inspiration Breath Hold Breast Irradiation", Int. Radiation Oncology Biol. Phys., vol. 78. No. 5, 2010, (pp. 1345-1351).

(Continued)

*Primary Examiner* — Mahendra R Patel
(74) *Attorney, Agent, or Firm* — Tucker Ellis LLP

(57) ABSTRACT

A computer-implemented medical data processing method for determining a difference in position of an imaged anatomical body part of a patient, the method comprising executing, on at least one processor of at least one computer, steps of: acquiring, at the at least one processor, first patient image data describing a digital image of a first anatomical body part during a first phase of inspiration and the position of the first anatomical body part during the first phase of inspiration in a first reference system associated with the first image data; acquiring, at the at least one processor, second patient image data different from the first patient image data and describing a digital image of the first anatomical body part during a second phase of inspiration and the position of the first anatomical body part during the second phase of inspiration in a second reference system associated with the second image data; acquiring, at the at least one processor, position transformation data describing a transformation between the first reference system and the (Continued)

second reference system; and determining, by the at least one processor and based on the first patient image data and the second patient image data and the position transformation data, position difference data describing a relative position between the position of the first anatomical body part during the first phase of inspiration and the position of the first anatomical body part during the second phase of inspiration.

20 Claims, 5 Drawing Sheets

(51) Int. Cl.
| | | |
|---|---|---|
| *G06T 7/30* | (2017.01) | |
| *G06T 7/73* | (2017.01) | |
| *G06T 7/246* | (2017.01) | |
| *A61B 5/00* | (2006.01) | |
| *A61N 5/10* | (2006.01) | |
| *A61B 34/10* | (2016.01) | |
| *G16H 30/40* | (2018.01) | |
| *G06T 7/00* | (2017.01) | |
| *G06T 11/00* | (2006.01) | |
| *A61B 90/00* | (2016.01) | |

(52) U.S. Cl.
CPC ......... *A61N 5/1037* (2013.01); *A61N 5/1039* (2013.01); *A61N 5/1049* (2013.01); *G06T 7/0014* (2013.01); *G06T 7/248* (2017.01); *G06T 7/251* (2017.01); *G06T 7/30* (2017.01); *G06T 7/74* (2017.01); *G06T 7/75* (2017.01); *G06T 11/003* (2013.01); *G16H 30/40* (2018.01); *A61B 2034/107* (2016.02); *A61B 2090/3762* (2016.02); *A61N 2005/1059* (2013.01); *G06T 2207/10072* (2013.01); *G06T 2207/10081* (2013.01); *G06T 2207/10116* (2013.01); *G06T 2207/20128* (2013.01); *G06T 2207/20221* (2013.01); *G06T 2207/30008* (2013.01); *G06T 2207/30081* (2013.01); *G06T 2207/30096* (2013.01); *G06T 2207/30196* (2013.01)

(58) Field of Classification Search
CPC ..................... G06T 7/75; G06T 11/003; G06T 2207/10072; G06T 2207/10081; G06T 2207/10116; G06T 2207/20128; G06T 2207/20221; G06T 2207/30008; G06T 2207/30081; G06T 2207/30096; G06T 2207/30196; A61B 5/0077; A61B 5/7292; A61B 34/10; A61B 2034/107; A61B 2090/3762; A61N 5/1037; A61N 5/1039; A61N 5/1049; A61N 2005/1059; G16H 30/40

USPC .............................................................. 60/1
See application file for complete search history.

(56) References Cited

U.S. PATENT DOCUMENTS

| | | | | |
|---|---|---|---|---|
| 7,693,563 | B2* | 4/2010 | Suresh ................... | G16H 30/20 600/407 |
| 7,889,906 | B2* | 2/2011 | Smith ................... | A61N 5/1049 382/294 |
| 7,998,062 | B2* | 8/2011 | Gilboa ................... | A61B 34/20 600/113 |
| 8,150,495 | B2* | 4/2012 | Edwards ............... | A61B 34/20 600/424 |
| 8,939,920 | B2* | 1/2015 | Maad ..................... | A61B 6/0487 600/595 |
| 10,292,619 | B2* | 5/2019 | Averbuch ................ | A61B 5/06 |
| 2011/0130644 | A1* | 6/2011 | Stemmer ............... | A61B 5/055 600/410 |
| 2013/0303887 | A1* | 11/2013 | Holsing ................. | A61B 34/20 600/109 |
| 2014/0275704 | A1* | 9/2014 | Zhang ................... | A61N 5/1067 600/1 |
| 2015/0305612 | A1* | 10/2015 | Hunter ................. | A61B 1/2676 600/109 |

FOREIGN PATENT DOCUMENTS

| | | | | |
|---|---|---|---|---|
| JP | | 4632535 B2 * | 2/2011 | .......... A61B 5/0263 |
| WO | WO-2016030470 A1 * | | 3/2016 | .......... A61B 5/1077 |

OTHER PUBLICATIONS

Latty et al., "Review of Deep Inspiration Breath-Hold Techniques for the Treatment of Breast Cancer", J. Med. Radiat Sci., 2015, (pp. 74-81).

Mageras et al., "Deep Inspiration Breath Hold and Respiratory Gating Strategies for Reducing Organ Motion in Radiation Treatment", Seminars in Radiation Oncology, vol. 14. No 1, Jan. 2004, (pp. 65-75).

Mittauer et al., "Monitoring ABC-Assisted Deep Inspiration Breath Hold for Left-Sided Breast Radiotherapy With an Optical Tracking System", Med. Phys. 42, Jan. 2015, (pp. 134-143).

Nehmeh et al., "Deep-Inspiration Breath-Hold PET/CT of the Thorax", The Journal of Nuclear Medicine, vol. 48, No. 1, Jan. 2007, (pp. 22-26).

D'Souza et al., "Real-Time Infra-Fraction-Motion Tracking Using the Treatment Couch: A Feasibility Study", Institute of Physics Publishing, vol. 50, 2005, (pp. 4021-4033).

International Search Report for corresponding international application No. PCT/EP2017/054323, dated Aug. 11, 2017.

* cited by examiner

DEEP INSPIRATION BREATH-HOLD SETUP USING X-RAY IMAGING

RELATED APPLICATION DATA

This application is a national phase application of International Application No. PCT/EP2017/054323 filed 24 Feb. 2017, the contents of which are incorporated herein by reference.

The present invention relates to a computer-implemented medical method for determining a difference in position of an imaged anatomical body part of a patient. The invention also relates to a computer configured to execute a program corresponding to the method and a medical system for determining the difference in position of the imaged anatomical body part, the system including the aforementioned computer.

TECHNICAL BACKGROUND

The treatment of breast cancer in most cases starts with a resection of the tumor, and is followed by radiation therapy. Clinical studies have shown that irradiating the tumor bed reduces the risk of recurrence dramatically. Negative side-effects are for example that the heart—especially the RIVA (ramus interventricularis anterior, a coronary vessel)—is very sensitive to radiation and thus the treatment may in the long term lead to heart diseases. This problem arises especially regarding treatment of the left breast, because in this case the distance from target to the heart is comparatively short. Therefore, these treatments are mostly performed in state of a deep inspiration breath-hold (DIBH). With inspiration, the heart moves away from the area to be treated in inferior and posterior direction, and thus the heart is moved out of the radiation beam's path.

The patient is coached to perform a deep inspiration breath hold during CT scanning. The treatment plan is created based on that CT scan. During treatment the patient is again coached to—as close as possible—reproduce the DIBH that was existent during CT scanning.

Previous solutions require a breathing signal at the CT scanner, or more general they require more information from planning/scanning than the usual planning data (CT data, treatment plan and anatomical structures). The baseline of free breathing and information about the breathing extent at the breath hold is used to make sure that the breath hold performed during treatment is close to the breath hold performed at CT scanning time.

The present invention is designed so that the usual planning data can be used whilst enjoying the benefits of a treatment during DIBH. The present invention is designed to provide a reliable method for determining a difference in position of an imaged anatomical body part of a patient.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method uses CT data acquired during a phase of deep inspiration breath hold. An optical position tracking system is used to track the surface of the patient. An outer contour of the CT data is matched with the tracked surface of the patient to determine whether the patient is in a state of deep inspiration breath hold. In this case, an x-ray image is acquired. The x-ray image data is then compared with the CT data to verify the state of deep inspiration breath hold. Deviations of positions of anatomical body parts which move during inspiration between the x-ray image data and the CT data are used to correct the tracked position of the patient surface or to shift a patient couch. Afterwards, the corrected tracked surface is used in combination with planning data and the CT data to determine the position of a treatment target based on the corrected tracked surface. A treatment beam can be (de)activated based on the tracking result, e.g. in case the state of deep inspiration breath hold is no longer maintained or in case the position of the patient has changed significantly.

GENERAL DESCRIPTION OF THE PRESENT INVENTION

In this section, a description of the general features of the present invention is given for example by referring to possible embodiments of the invention.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can for example be added to said other embodiment.

According to a first aspect of the present invention, a computer-implemented medical method (for example, a data processing method) is provided for determining a difference in position of an imaged anatomical body part of a patient. The method for example comprises executing, on at least one processor of at least one computer, a step of acquiring, at the at least one processor, first patient image data. The first patient image data is for example three-dimensional image data, for example computed x-ray tomography data (CT data) or three-dimensional ultrasonic data or tomographic magnetic resonance data (MR data or MRT data). The first patient image data for example describes (for example, represents or defines) a digital image. The digital image is an image of a first anatomical body part and a second anatomical body part and a third anatomical body part during a first phase of inspiration. The first anatomical body part is for example at least partly different in at least one of function or anatomy from the second anatomical body part. The third anatomical body part is for example at least partly different in at least one of function or anatomy from the first anatomical body part and at least partly different in at least one of function or anatomy from the second anatomical body part. For example, the first anatomical body part is a body part moving during inspiration, for example comprising at least one of the following:

body of sternum;
manubrium of sternum;
xiphoid process;

one or more anterior ribs;
one or more costal cartilages;
one or more fiducial markers.

For example, the second anatomical body part is a body part not moving during inspiration, for example comprising at least one of the following:
one or more vertebrae;
one or more posterior ribs;
one or more fiducial markers.

The first phase of inspiration is for example a phase of deep inspiration breath hold at a first point in time. For example, the first image data has been obtained using imaging methods at this first point in time.

The first patient image data also describes (for example, represents or defines) the position of the first anatomical body part and the position of the second anatomical body part and the position of the third anatomical body part during the first phase of inspiration in a first reference system. For example, the positions are not directly included in the imaging data, but the corresponding anatomical body parts are at least partly included in the imaged area and are thus at least partly included in the imaging data. Alternatively or additionally, the positions are described by one or more vectors or vector functions defined in the first reference system. The "position" may but does not need to denote a single point in a reference system, and may alternatively or additionally denote a specific area or volume in a reference system. The first reference system may be associated with the first image data. For example, this association is made by using a specific tag included in the image data, for example a DICOM header. For example, the first reference system is set when obtaining the first image data using the imaging methods. For example, the first reference system may be set by an imaging system when acquiring the image data, for example setting the isocenter used for imaging as origin of the first reference system.

The method for example further includes acquiring, at the at least one processor, second patient image data. The second patient image data is for example different from the first patient image data. For example, the second patient image data is two-dimensional image data, for example radiographic x-ray image data or ultrasonic image data. The second image data for example describes (for example, represents or defines) a digital image of the first anatomical body part during a second phase of inspiration. For example, the second phase of inspiration is a phase of deep inspiration breath hold at a second point in time. The second point in time is for example later than the first point in time. The second image data for example also describes (for example, represents or defines) the position of the first anatomical body part during the second phase of inspiration in a second reference system. The second reference system is for example associated with the second image data in a way similar to that described above for the first image data and the first reference system. The first reference system is for example different from the second reference system.

The method for example further includes acquiring, at the at least one processor, position transformation data describing a transformation between the first reference system and the second reference system. Such a transformation is for example a rule that describes (for example, represents or defines) a relation (such as a transformation of bases) between the two different coordinate systems and points in them. For example, the relation is defined by a transformation matrix. The transformation may for example be split into different parts such as rotational and translational transformation components.

The method for example further comprises determining, by the at least one processor and based on the first patient image data and the second patient image data and the position transformation data, position difference data describing a relative position between the position of the first anatomical body part during the first phase of inspiration and the position of the first anatomical body part during the second phase of inspiration. For example, the position of the first anatomical body part (e.g. body of sternum) in the second patient image data (e.g. x-ray data) is determined. For example, the position of the first anatomical body part (e.g. body of sternum) in the first patient image data (e.g. deep inspiration breath hold (DIBH) CT data) is determined and the determined position is transformed from the first reference system (e.g. reference system associated with DIBH CT data) into the second reference system (e.g. associated with x-ray data). For example, the so transformed position is compared with the position of the first anatomical body part in the second reference system. The result of the comparison is for example described (for example, represented or defined) by the position difference data. The position difference data for example comprises transformation data and/or one or more vectors and/or vector functions.

Alternatively or additionally, an image fusion algorithm may be used to match the first anatomical body part in the second patient image data with the first patient image data. This match results in a transformation describing the matching result. This transformation can be used together with the position transformation data to compare the position of the first anatomical body part in the first patient image data with the position of the first anatomical body part in the second patient image data under a common reference. The result of this comparison is for example described (for example, represented or defined) by the position difference data. The position difference data for example comprises transformation data and/or one or more vectors and/or vector functions.

To determine the position of the first anatomical body part in the first patient image data and/or in the second patient image data, for example atlas data is used. For example, the atlas data describes (for example, represents or defines) the position of the first anatomical body part in a reference body model. The reference body model is for example obtained by segmenting scan data from a plurality of patients and averaging the segmentation results. The first patient image data and/or the second patient image data is for example segmented and compared with the atlas data. For example, an image fusion algorithm is used to match the segmented parts of the first patient image data and/or of the second patient image data with the atlas data. For example, matched segmented areas are assumed to represent the same anatomical structures. Alternatively or additionally, a user selects the position of the first anatomical body part in the first patient image data and/or in the second patient image data.

Before acquiring the second patient image data, the method for example includes a step of acquiring, at the at least one processor, third patient image data. For example, the third patient image data is two-dimensional image data, for example radiographic x-ray image data or ultrasonic image data. The third patient image data is for example different from the first patient image data and/or the second patient image data. It for example describes (for example, represents or defines) a digital image of the second anatomical body part during a third phase of inspiration. The third phase of inspiration is for example an arbitrary phase of inspiration of the patient, and in one specific example is a phase of deep inspiration breath hold. The third phase of inspiration is for example a phase of inspiration at a third point in time, which is for example later than the first point in time and/or earlier than the second point in time. The third patient image data for example additionally describes (for example, represents or defines) the position of the second anatomical body part in the second reference system during the third phase of inspiration.

The method in one example further includes a subsequent step of determining, by the at least one processor and based on the first patient image data and the third patient image data, the position transformation data. For example, the position of the second anatomical body part (e.g. vertebrae) in the third patient image data (e.g. x-ray data) is determined. For example, the position of the second anatomical body part (e.g. vertebrae) in the first patient image data (e.g. DIBH CT data) is determined and the determined position is transformed from the first reference system (e.g. reference system associated with DIBH CT data) into the second reference system (e.g. associated with x-ray data). For example, the position so transformed is compared with the position of the second anatomical body part in the second reference system. For example, the result of the comparison is described (for example, represented or defined) by the position transformation data. Alternatively or additionally, an image fusion algorithm may be used to match the second anatomical body part in the third patient image data with the first patient image data. This match results in a transformation describing the matching result. This transformation is for example described (for example, represented or defined) by the position transformation data.

The position of the second anatomical body part in the third patient image data or in the first patient image data is for example determined based on atlas data. For example, atlas data describing a model of the second anatomical body part in a reference body is acquired at the at least one processor for this purpose. The reference body may be obtained by segmenting image data from a plurality of patients and averaging the results. For example, the third patient image data or the first patient image data is segmented and the segmentation results are compared with the atlas data. For this comparison, for example image fusion is used to match the second anatomical body part of the atlas data with the third patient image data or the first patient image data. A segmented region in the first patient image data which matches the second anatomical body part of the atlas data adequately is for example identified as the second anatomical body part in the first patient image data and its position in the first reference system is determined. A segmented region in the third patient image data which matches the second anatomical body part of the atlas data adequately is for example identified as the second anatomical body part in the third patient image data and its position in the second reference system is determined.

In a further example, the method includes a step of determining, by the at least one processor and based on the position transformation data and after determining the position transformation data, control data describing a control command for controlling a patient support device to be moved according to the transformation. For example, the position transformation data describes a large deviation between the position of the second anatomical body part in the first reference system and the second reference system. To compensate for this deviation, a correctional movement can be applied to the patient couch. Alternatively or additionally, a correctional movement may be applied to a treatment device used for treatment or a correctional offset may be applied to planning data which for example describes (for example, represents or defines) the position of a target to be treated in the first reference system.

To obtain the position transformation data, another approach is possible using only the first patient image data and the second image data and not the third patient image data. According to this approach, the second patient image data describes (for example, represents or defines) a digital image of the first anatomical body part and the second anatomical body part during the second phase of inspiration. The second patient image data for example further describes the position of the first anatomical body part and the position of the second anatomical body part during the second phase of inspiration in the second reference system.

According to this approach, after acquiring the second patient image data, the position transformation data is determined, by the at least one processor, based on the first image data and the second image data. For example, the position of the second anatomical body part in the first patient image data and in the second patient image data may be used. For example, the position of the second anatomical body part (e.g. vertebrae) in the second patient image data (e.g. x-ray data) is determined. For example, the position of the second anatomical body part (e.g. vertebrae) in the first patient image data (e.g. DIBH CT data) is determined and the determined position is transformed from the first reference system (e.g. reference system associated with DIBH CT data) into the second reference system (e.g. associated with x-ray data). For example, the position so transformed is compared with the position of the second anatomical body part in the second reference system. For example, the result of the comparison is described (for example, represented or defined) by the position transformation data. Alternatively or additionally, an image fusion algorithm may be used to match the second anatomical body part in the second patient image data with the first patient image data. This match results in a transformation describing the matching result. This transformation is for example described (for example, represented or defined) by the position transformation data.

Also in case of this approach, atlas data describing a model of the second anatomical body part in a reference body may be acquired at the at least one processor. The position transformation data may thereafter be determined, by the at least one processor, based on the first patient image data and the second patient image data and the atlas data. For example, the atlas data is used to determine the position of the second anatomical body part in the first and/or in the second patient image data. For example, atlas data describing a model of the second anatomical body part in a reference body is acquired at the at least one processor for this purpose. The reference body may be obtained by segmenting image data from a plurality of patients and averaging the results. For example, the first patient image data or the second patient image data is segmented and the segmentation results are compared with the atlas data. For this comparison, for example image fusion is used to match the second anatomical body part of the atlas data with the second patient image data or the first patient image data. A segmented region in the first patient image data which matches the second anatomical body part of the atlas data adequately is for example identified as the second anatomical body part in the first patient image data and its position in the first reference system is determined. A segmented region in the second patient image data which matches the second anatomical body part of the atlas data adequately is for example identified as the second anatomical body part in the second patient image data and its position in the second reference system is determined.

In another example, the method further comprises, before acquiring the second patient image data, a step of acquiring, at the at least one processor, patient surface data describing the position of a surface of the patient in a third reference system associated with an optical position tracking system. For example, the patient surface data is acquired based on using an optical position tracking system, for example by tracking a predetermined region of the surface of the patient which moves during inspiration, for example a region close to the sternum. For example, the predetermined region is a region which is not subject to biological changes during treatment such as swelling. For example, that the region should in case of treatment of the left breast not include the left breast entirely since the left breast tends to swell significantly during treatment. The optical position tracking system for example uses at least one of patterned light (structured light), infrared light and one or more optical markers or multiple cameras. The patient is for example irradiated with patterned light and a camera acquires an image of the surface of the patient which is irradiated with the patterned light. The image data describing (for example, representing or defining) the surface of the patient is for example referred to as patient surface data. Alternatively or additionally, the optical position tracking system determines, based on the image data describing the surface of the patient, the position of the surface of the patient in the third reference system. For example, data describing the determined position may be referred to as patient surface data. In another example, the patient is not irradiated with patterned light but optical markers are placed on the surface of the patient. Also in this example, a camera acquires an image of the surface of the patient including the optical markers. The image data describing (for example, representing or defining) the surface of the patient is for example referred to as patient surface data. Alternatively or additionally, the optical position tracking system determines, based on the image data describing the surface of the patient, the position of the surface of the patient in the third reference system. For example, data describing (for example, representing or defining) the determined position may be referred to as patient surface data. In another example, multiple cameras are used to acquire a plurality of images of the surface of the patient from different points of view. In this example, the correlation of one camera to another is known, i.e. transformations between the reference systems of the plurality of cameras are known in advance. The image data describing (for example, representing or defining) the surface of the patient is for example referred to as patient surface data. Alternatively or additionally, the optical position tracking system determines, based on the image data describing the surface of the patient and based on the transformations between the reference systems of the plurality of cameras, the position of the surface of the patient in the third reference system. For example, data describing the determined position may be referred to as patient surface data.

After acquiring the patient surface data, the method for example comprises a step of acquiring, at the at least one processor, surface offset data describing (for example, representing or defining) a value of an offset between the position of the patient surface described (for example, represented or defined) by the acquired patient surface data and a second position of the patient surface. The value of an offset is for example equal to zero as default, but may be overwritten during subsequent method steps as will be noted below. The second position of the patient surface is for example a position of the patient surface described (for example, represented or defined) by the acquired patient surface data which is offset by a certain offset value as will be described below.

The method in one example further includes a subsequent step of determining, by the at least one processor and based on the patient surface data and the surface offset data, corrected patient surface data describing (for example, representing or defining) the corrected position of the surface of the patient. In case the surface offset value is equal to zero, the corrected position of the patient surface described (for example, represented or defined) by the corrected patient surface data is identical to the position of the patient surface described (for example, represented or defined) by the patient surface data. However, in case the surface offset value is not equal to zero, the corrected position of the patient surface described (for example, represented or defined) by the corrected patient surface data differs from the position of the patient surface described (for example, represented or defined) by the patient surface data in that it includes an offset.

In a next step, the method for example includes acquiring, at the at least one processor, the position transformation data mentioned above and acquiring, at the at least one processor, first camera position transformation data describing a transformation between the third reference system (e.g. associated with the optical position tracking system) and the second reference system (e.g. associated with the second patient image data and/or the third patient image data).

In a subsequent step, the method in one example includes determining, by the at least one processor and based on the first camera position transformation data and the position transformation data (e.g. describing a transformation between the first reference system and the second reference system), second camera position transformation data describing a transformation between the first reference system (e.g. associated with the first patient image data) and the third reference system (e.g. associated with the optical position tracking system).

Following this step, the method in one example further includes a step of determining, by the at least one processor and based on the corrected patient surface data and the second camera position transformation data and the first patient image data, surface transformation data describing a transformation between the corrected position of the surface of the patient and an outer contour of the first patient image data. For example, an outer contour of the first patient image data is obtained by determining an abrupt junction in the first patient image data, at which the image information drastically differs from a region outside the imaged patient body. For example, the outer contour represents a surface of the patient in the first patient image data. Many methods for determining such an outer contour in the first patient image data are possible, for example using image contrast, pattern recognition or atlas data. The position of the outer contour is for example determined as a position in the first reference system. The position of the (corrected) patient surface is for example given in a third reference system by (corrected) patient surface data as noted above. The second camera position transformation data for example describes (for example, represents or defines) a transformation between the first and the third reference system as noted earlier. As noted above with respect to the determination of the position transformation data and the position difference data, different ways may be used to obtain a transformation between positions of anatomical body parts in two different reference systems. For example, one of these methods is used to determine the surface transformation data. For example, the corrected position of the surface of the patient and the position of the outer contour in the first patient image data may be used for that purpose. As noted above, for example an image fusion algorithm is used to match the surface of the patient with the outer contour. The fusion result, i.e. the required shift between the first and the third reference system to obtain the match, for example represents the surface transformation data.

After determining the surface transformation data and before acquiring the second patient image data, the method for example further comprises a step of determining, by the at least one processor and based on the surface transformation data, inspiration phase data. The inspiration phase data may describe (for example, represent or define) a phase of inspiration of the patient. For example, the inspiration phase data may indicate whether a phase of deep inspiration breath hold is reached which is sufficiently similar to the first phase of inspiration. This may be assumed to be the case when the surface transformation data describes (for example, represents or defines) a minimal difference between the corrected position of the surface of the patient and an outer contour of the first patient image data.

For example, the method further comprises, after determining the inspiration phase data and before acquiring the second patient image data, a step of determining, by the at least one processor and based on the inspiration phase data, control data describing (for example, representing or defining) a control signal for controlling a medical imaging device to acquire the second patient image data. For example, the control data describes (for example, represents or defines) a control signal for controlling the medical imaging device to acquire the second patient image data a short waiting period, for example a few seconds (1-10 seconds), after the inspiration phase data indicates that a phase of deep inspiration breath hold is reached or at the precise time this phase is reached. The control data describing (for example, representing or defining) a control signal for controlling a medical imaging device for example only describes (for example, represents or defines) a control signal for controlling a medical device to acquire an image in case other conditions are met such as stability of the breathing phase for a certain period of time or else. The medical imaging device is for example an x-ray apparatus configured to acquire at least one x-ray image.

After acquiring the surface transformation data, the method for example further comprises a step of acquiring, at the at least one processor, planning data describing (for example, representing or defining) the position of the third anatomical body part in the first reference system. For example, the planning data describes (for example, represents or defines) the position and/or geometry of the third anatomical body part in the first reference system associated with the first patient image data. The planning data is for example prepared by a user by selecting a certain region/volume in the first patient image data. Alternatively or additionally, the selection may be supported by a segmentation algorithm.

Alternatively or additionally, atlas data may be used to determine the position of the third anatomical body part in the first patient image data. For example, atlas data describing a model of a reference body may be acquired, which is obtained by acquiring image data of a plurality of patients and averaging the results. For example, the atlas data represents a model of a healthy reference body. For example, the first patient image data is matched with the atlas data to identify anatomical structures in the first patient image data. For example, a region or volume in the first patient image data is identified which deviates significantly from the atlas data in case a special anatomical part such as a tumor is present in the first patient image data. This special anatomical part is for example identified as the third anatomical body part. The third anatomical body part may be a target for treatment such as a tumor.

The method in one example comprises a subsequent step of determining, by the at least one processor and based on the corrected patient surface data and the surface transformation data and the planning data, target position data. The planning data for example describes (for example, represents or defines) the position of a target in the first reference system. The corrected patient surface data is for example obtained based on using at least the optical position tracking system mentioned earlier. The target position data for example describes (for example, represent or define) the relative position between the third anatomical body part (such as a target) and the corrected position of the surface of the patient. To obtain the target position data, a transformation between the third reference system and the first reference system is necessary. In this example, the surface transformation data is used for that purpose, for example together with the surface offset data. Since in this example all necessary transformations between the position of the third anatomical body part in the first reference system and the corrected position of the surface of the patient in the third reference system are known, the position of the third anatomical body part such as a target can be tracked in real time by tracking the patient surface (using the corrected position of the surface of the patient) and determining the position of the target based on the target position data.

The method for example further comprises a step of acquiring, at the at least one processor, difference threshold data describing thresholds of the position difference data performed after determining the position difference data. The difference threshold data for example includes maximum values for rotational and/or translational components of the position difference data. For example, the difference threshold data may include a first predetermined difference threshold and a second predetermined difference threshold. The first predetermined difference threshold for example includes a maximum value of an offset of the position of the second anatomical body part in the first patient image data compared with the position of the second anatomical body part in the second patient image data in a breathing direction, for example a few millimeters, such as 3 or 4 mm. The second predetermined difference threshold for example includes a maximum value of an offset of the position of the second anatomical body part in the first patient image data compared with the position of the second anatomical body part in the second patient image data in a direction different from the breathing direction (for example left/right side of the patient), for example a few millimeters, such as 5 mm. These offset values for example indicate how well the second phase of inspiration at the second point in time corresponds to the first phase of inspiration at the first point in time.

As a subsequent step, the method for example comprises determining, by the at least one processor and based on the difference threshold data and the position difference data, first condition data. The first condition data for example describes (for example, represents or defines) whether the position difference data exceeds the first predetermined difference threshold. For example, the first condition data is data representing a binary state, for example true or false. If the first condition data describes (for example, represents or defines) that the position difference data exceeds the first predetermined difference threshold, this for example means that the second phase of inspiration at the second point in time does not correspond acceptably to the first phase of inspiration at the first point in time. In this case, the tracked position of the patient is for example corrected to compensate an offset in a breathing direction. This is for example done by determining, by the at least one processor and based on the position difference data, the surface offset data. As noted earlier, this surface offset data is for example used to determine the corrected position of the surface of the patient. For example, the previous value of the surface offset data, such as for example a default value of zero, is overwritten in this step. In this example, the position of the surface of the patient described (for example, represented or defined) by the patient surface data is offset by the new offset value of the surface offset data to obtain the corrected position of the surface of the patient described (for example, represented or defined) by the corrected patient surface data. Using the corrected position of the surface of the patient, for example the breathing phase may be determined. In this example, based on the breathing phase, additional patient image data may be acquired in case a phase of deep inspiration breath hold is reached. For example, the method may be repeated, starting at acquiring the patient surface data. Alternatively, the additional patient image data may be acquired independent from the breathing phase. In this case, the method may be repeated starting at acquiring the second patient image data.

If the first condition data describes (for example, represents or defines) that the position difference data does not exceed the first predetermined difference threshold, the method continues for example with a step of determining, by the at least one processor and based on the target position data and the corrected patient surface data and the inspiration phase data, treatment parameter data. The treatment parameter data for example describes (for example, represents or defines) at least one treatment parameter of a treatment device. For example, the treatment parameter data describes (for example, represents or defines) the position of a third anatomical body part (e.g. a target) in the third reference system depending on the breathing movements of the patient. For example, the treatment parameter data may include control parameters to control a treatment device such as a radiotherapy or a radiosurgery device. For example, the control parameters may include information on the position and/or (de)activation time of at least one treatment beam to be emitted from the treatment device. For example, the control parameters include information on the beam arrangement, the beam position or the beam line. The at least one treatment parameter for example describe (for example, represent or define) deactivation of the treatment device in case the inspiration phase data indicates a predetermined inspiration phase is reached which is not intended for treatment (e.g. gating of treatment device based on breathing phase). The at least one treatment parameter may alternatively or additionally describe (for example, represent or define) deactivation of the treatment device in case the patient surface data indicates a predetermined position of the surface of the patient is reached which is not intended for treatment (e.g. interlock based on patient position).

The method in one example further comprises a step of determining, after acquiring the difference threshold data, by the at least one processor and based on the difference threshold data and the position difference data, second condition data. The second condition data for example describes (for example, represents or defines) whether the position difference data exceeds the second predetermined difference threshold noted earlier. For example, this may be the case if the patient is positioned during the second point in time different than during the first point in time. Such a different positioning of the patient for example results in a deviation of the position of the second anatomical body part in the first patient image data compared with the position of the second anatomical body part in the second patient image data in a direction other than the breathing direction. For example, such an offset may be compensated not by applying a value of an offset to the position of the surface of the patient to obtain the corrected position of the surface of the patient, but by shifting the position of the patient couch and/or the treatment device. For this reason, the method for example further includes a step of determining, by the at least one processor and based on the position difference data, control data describing (for example, representing or defining) a control command for controlling a patient support device and/or a treatment device to be moved according to the position difference data, if the second condition data describes (for example, represents or defines) that the position difference data exceeds the second predetermined difference threshold. For example, the movement of the patient support device and/or treatment device is taken into account in subsequent method steps, i.e. when acquiring data or when determining data. For example, this shift is added to, subtracted from or used as a transformation for one or more of the data used in subsequent steps of the method.

If the second condition data describes (for example, represents or defines) that the position difference data does not exceed the second predetermined difference threshold and if the first condition data describes (for example, represents or defines) that the position difference data does not exceed the first predetermined difference threshold, the method may continue with the aforementioned step of determining the treatment parameter data. For example, this is a step of determining, by the at least one processor and based on the target position data and the patient surface data and the inspiration phase data, treatment parameter data describing at least one treatment parameter of a treatment device.

The method in one example further comprises a step of outputting, by the at least one processor, the treatment parameter data to a treatment device. For example, this step is performed after the treatment parameter data has been determined. For example, the treatment parameter data is output via a wire or wirelessly, directly or via intermediary structures such as routers and/or cloud computing systems and in an analog or digital format.

For verification of the corrected position of the surface of the patient, the method is for example repeated after determining the treatment data, starting at acquiring the patient surface data or at acquiring the second patient image data. Such verification using for example additional x-ray image data is for example performed upon being triggered by a user or automatically, for example in case a certain movement of the surface of the patient is detected with the optical position tracking system or in case a predetermined period of time has lapsed.

According to a second aspect, the method is for example implemented as a computer program which, when running on at least one processor of at least one computer or when loaded into the memory of at least one computer, causes the at least one computer to perform the method according to the first aspect. For example, all the steps or merely some of the steps (i.e. less than the total number of steps) of the method in accordance with the first aspect can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method according to the first aspect.

According to a third aspect, a signal wave is provided, for example a digital signal wave, carrying information which represents the program according to the second aspect.

According to a fourth aspect, a non-transitory computer-readable program storage medium is provided on which the program according to the second aspect is stored.

According to a fifth aspect, at least one computer is provided. The computer for example comprises at least one processor and a memory, wherein the program according to the second aspect is running on the at least one processor or is loaded into the memory, or wherein the at least one computer comprises the program storage medium according to the fourth aspect.

According to a sixth aspect, a system for supporting determining a difference in position of an imaged anatomical body part of a patient is provided. For example, the system comprises the computer according to the fifth aspect. For example, the system may further comprise a medical imaging device, for example a CT scanner or an x-ray device for acquiring patient image data. The medical imaging device may be operably coupled to the at least one computer for transmitting a signal to the at least one computer corresponding to the patient image data, wherein the patient image data is at least one of the first patient image data, the second patient image data and third patient image data.

The system of the sixth aspect for example further comprises an optical position tracking system for acquiring the patient surface data describing the position of the surface of the patient. The optical position tracking system may be operably coupled to the at least one computer for transmitting a signal to the at least one computer corresponding to the patient surface data.

The system for example further comprises a treatment device such as a radiotherapy and/or radiosurgery device. The treatment device is for example operably coupled to the at least one computer for receiving a signal from the at least one computer corresponding to treatment parameter data describing (for example, representing or defining) at least one of activation or deactivation of a treatment device. As noted earlier, the treatment parameter data for example includes additional information, for example indicating a position and/or intensity and/or time protocol of a treatment beam to be emitted.

The system for example further comprises a patient support device such as a patient couch. The patient support device is for example operably coupled to the at least one computer for receiving a signal from the at least one computer corresponding to control data describing (for example, representing or defining) a control command for controlling the patient support device to be moved. As noted earlier, a positioning of the patient support device may be performed in case the difference data exceeds the second predetermined difference threshold.

In the following, definitions are given which are being used throughout this disclosure.

Definitions

In this section, definitions for specific terminology used in this disclosure are offered which also form part of the present disclosure.

The computer of the fifth aspect for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the World Wide Web (WWW) and located in a so-called cloud of computers which are all connected to the World Wide Web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (World Wide Web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate/reference system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The method of the first aspect for example relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionizing radiation is for example used for the purpose of treatment. For example, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumor are treated using ionizing radiation. The tumor is then an example of a treatment body part. A treatment body part may for example be referred to as target and/or third anatomical body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: https://www.elekta.com/radiotherapy/treatment-solutions/elekta-vmat.html and https://www.varian.com/oncology/treatment-techniques/external-beam-radiation/vmat.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 is a flow diagram illustrating the basic steps of the disclosed method, which in the illustrative example of FIG. 1 starts with a step S1.1 of acquiring the first patient image data. In subsequent step S1.2, the second patient image data is acquired. Step S1.3 then continues with acquiring the position transformation data, followed by step S1.4 which encompasses determining the position difference data based on the data acquired in preceding steps S1.1 to 1.3.

FIG. 2 shows a first sequence of steps according to a specific embodiment of the disclosed method. In step S2.1, a diagnostic scan of a patient in a phase of deep inspiration breath hold (DIBH) is performed. This scan data may for example be referred to as first patient image data. In step S2.2, a user performs planning and contouring on the DIBH CT scan. For example, a region to be treated such as a tumor may be selected by the user, for example with the help of atlas data. The region to be treated may be referred to as third anatomical body part or target. The data indicating the planning performed by the user may be referred to as planning data. In step S2.3, the patient is positioned on a treatment couch. Next, in step S2.4, an x-ray image pair of the patient in free breathing state is acquired. This may be referred to as third patient image data. In step S2.5, the x-ray image pair is fused to bony structures of the DIBH CT using image fusion. The bony structures are structures not moving with respiration (e.g. spine or posterior ribs). These bony structures may be referred to as second anatomical body parts. In a next step, the DIBH CT and the x-ray image pair are registered to one another, meaning a transformation between the first reference system (associated with the DIBH CT scan) and the second reference system (associated with the x-ray images) is based on a matching result of an image fusion of the bony structures in the DIBH CT scan data and the bony structures in the x-ray image data. This transformation data may be referred to as position transformation data. In step S2.6, the fusion result, i.e. the obtained transformation, is applied to the treatment couch. This equalizes the position of the non-moving bony structures in the first reference system with the position of the non-moving bony structures in the second reference system since the two reference systems are transformed so as to be identical.

In step 2.7, a surface camera is used to obtain a live surface of the patient. The surface camera is one example of an optical position tracking system and may be used to acquire patient surface data describing (for example, representing or defining) a position of the surface of the patient. In step 2.8, a region of interest (ROI) is defined on the live surface to track the breathing motion of the patient and to track unexpected patient movements. For example, a predetermined region of the surface of the patient which moves during inspiration might be tracked, for example a region close to the sternum. The method thereafter continues with step S3.1 shown in FIG. 3.

Figure 1:
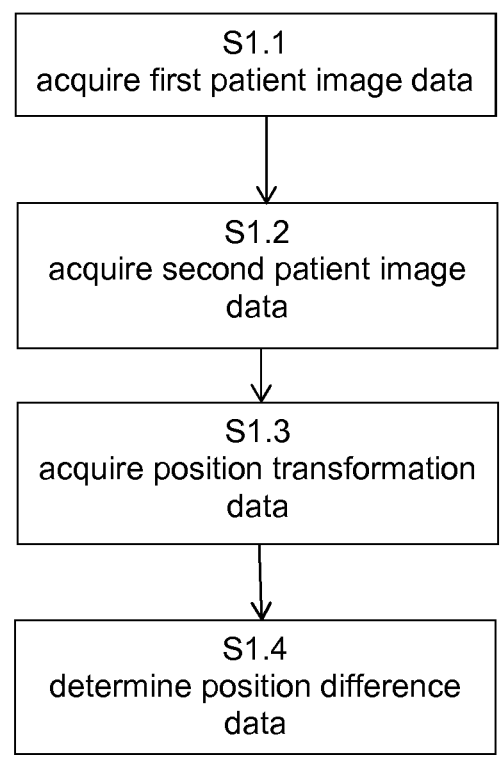
FIG. 1 is a flow diagram showing the basic steps of the disclosed method.
Figure 2:
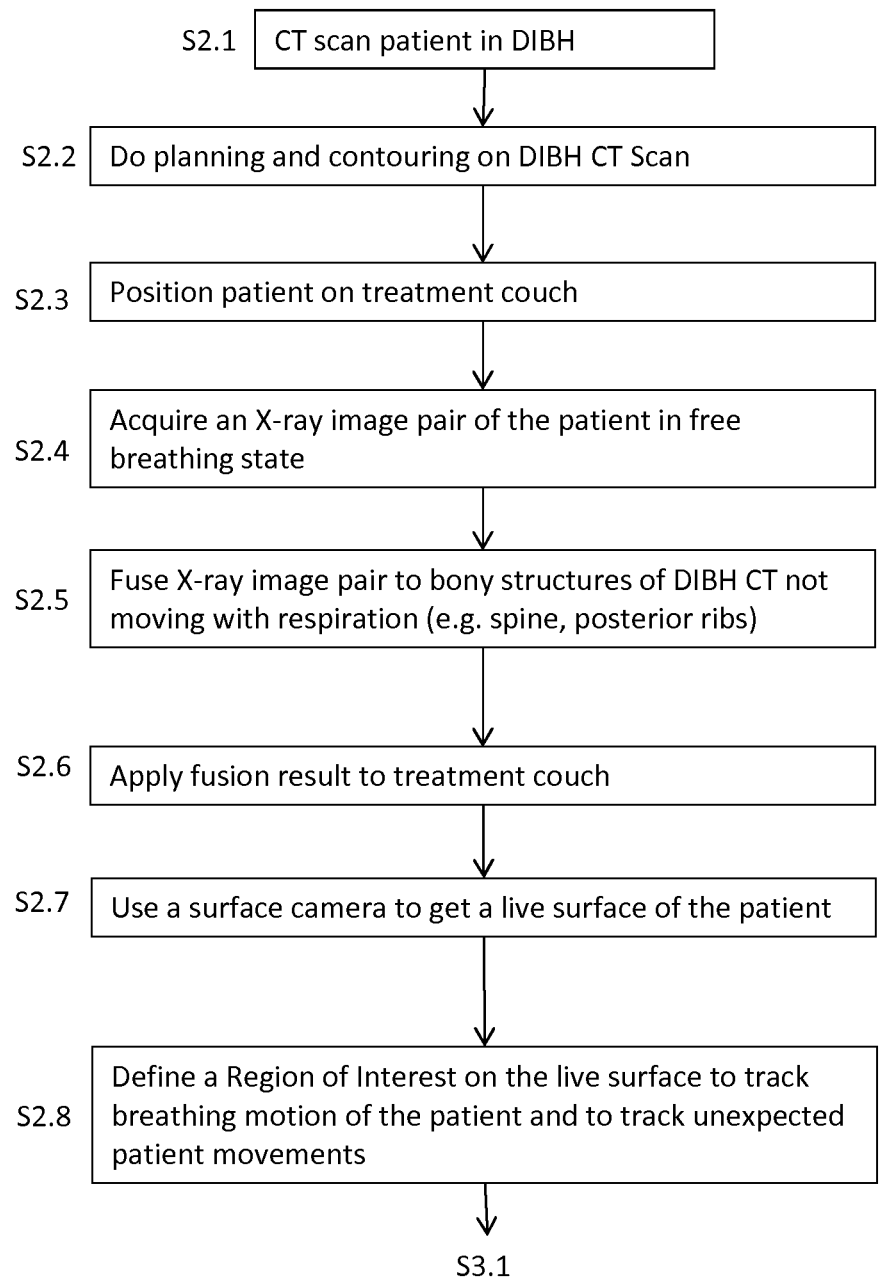
FIG. 2 shows a first sequence of steps of a specific embodiment of the disclosed method.
Figure 3:
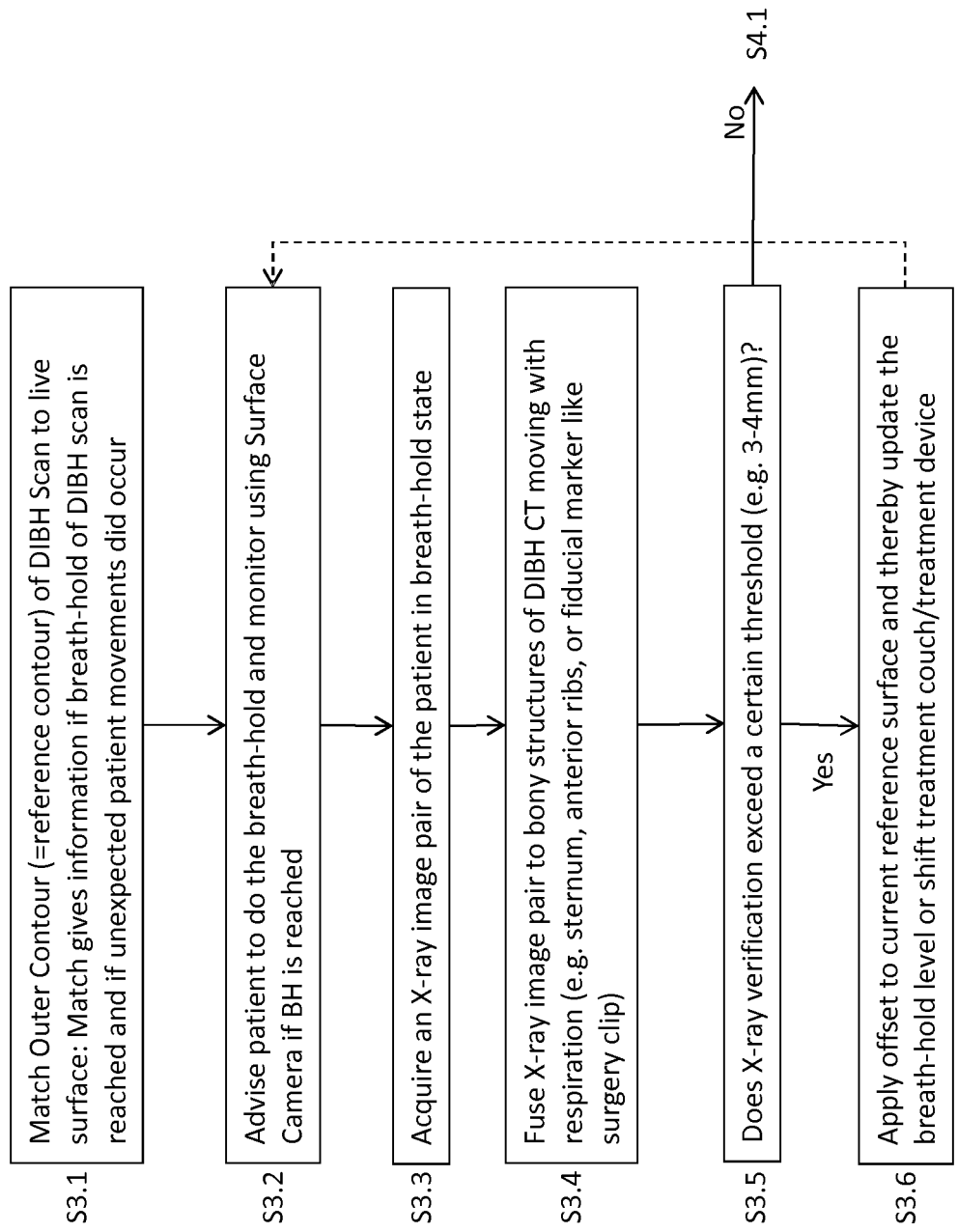
FIG. 3 shows a second sequence of steps of a specific embodiment of the disclosed method.

FIG. 3 shows a second sequence of steps of the specific embodiment of the disclosed method starting with step S3.1 which follows step S2.8 shown in FIG. 2.

In step S3.1, an outer contour (reference contour) of the DIBH CT scan is matched to the live surface. The matching is for example performed by using an image fusion algorithm (surface matching). For example, an Iterative Closest Point (ICP) algorithm may be chosen as surface matching algorithm. Iterative Closest Point (ICP) is an algorithm employed to minimize the difference between two clouds of points. ICP is for example often used to reconstruct 2D or 3D surfaces from different scans. In the ICP algorithm, one point cloud, the reference, or target, is kept fixed, while the other one, the source, is transformed to best match the reference. The algorithm iteratively revises the transformation (combination of translation and rotation) needed to minimize the distance from the source to the reference point cloud. The match may be described (for example, represented or defined) by surface transformation data. This match gives information if the phase of deep inspiration breath hold in which the patient was during acquisition of the DIBH CT scan (at first point in time) is reached. The match also gives information if unexpected patient movements did occur. For example, inspiration phase data may be determined as noted earlier. In step S3.2, the patient is advised to do the deep inspiration breath hold. Using the surface camera, it is monitored if this phase is reached. For example, the patient may be given visual information indicating the current phase of inspiration and the phase of inspiration to be reached. If the patient is in a phase of deep inspiration breath hold (step S3.3), an x-ray image pair of the patient is acquired, for example automatically. This may be referred to as second patient image data. The x-ray image pair is fused to bony structures moving with respiration (e.g. sternum, anterior ribs) or to a fiducial marker such as a surgery clip. These moving structures may be referred to as second anatomical body parts. The fusion result, which may be described (for example, represented or defined) by position difference data such as transformation data, for example one or more vectors and/or matrices, is compared with predetermined threshold values in step S3.5. These threshold values may be comprised in threshold difference data which is acquired and includes a first predetermined difference threshold and a second predetermined difference threshold. In case the x-ray verification (the position difference data) exceeds the first predetermined difference threshold in a breathing direction (Yes), an offset is applied to the current reference surface in step S3.6 which corresponds to the offset in the breathing direction indicated by the position difference data. This means that a corrected patient surface is obtained by applying the offset value to the tracked position of the patient surface (the live surface). Thereby, the breath-hold level is being updated. In case the x-ray verification (the position difference data) exceeds a second predetermined difference threshold in a direction different from the breathing direction (Yes), the treatment couch and/or the treatment device is shifted to compensate this offset (S3.6). After step S3.6, the method is repeated starting at step S3.2. In case the x-ray verification (the position difference data) does not exceed a certain threshold (No), the method continues with step S4.1 shown in FIG. 4.

Figure 4:
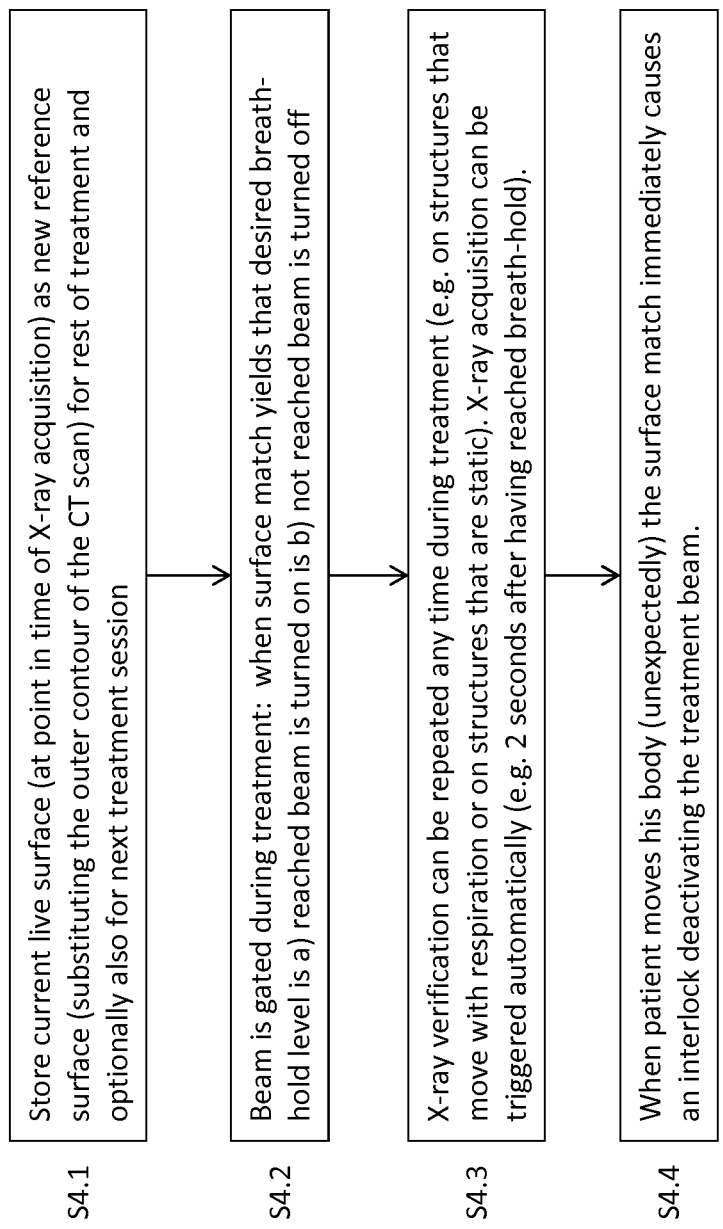
FIG. 4 shows a third sequence of steps of a specific embodiment of the disclosed method.

FIG. 4 shows a third sequence of steps of the specific embodiment of the disclosed method starting at step S4.1. In this step, the current live surface (at second point in time which is the point in time of x-ray acquisition at step S3.3) is stored as new reference surface, substituting the outer contour of the CT scan. The so obtained new reference surface may be referred to as corrected patient surface. The new reference surface is used for the rest of treatment and optionally also for a next treatment session. For example, the target position data may be used to determine the position of the target in relation to the new reference, enabling a tracking of the position of the target in dependence of the movement of the patient surface. In step S4.2, the treatment beam is gated during treatment. When the surface match, which is for example obtained using an ICP algorithm, yields that desired breath-hold level is reached, the treatment beam is turned on. For example, inspiration phase data can be used for this determination. If the desired breath-hold level is not reached, the treatment beam is turned off, preventing treatment during predetermined breathing phases, for example during a phase of exhalation.

In step S4.3, the x-ray verification (steps S3.2 to S3.5) is repeated during treatment, e.g. on structures that move with respiration (e.g. the second anatomical body parts) or on structures that are static (i.e. not moving with respiration, for example the first anatomical body parts). Also in this case, the x-ray acquisition can be triggered automatically, e.g. 2 seconds after having reached the breath-hold level. In case the patient moves his body unexpectedly (step S4.4), the surface match, which is for example obtained using an ICP algorithm, immediately causes an interlock deactivating the treatment beam.

According to the method disclosed herein, no additional hardware or additional CT scan is required. The requirements are for example just as usual: a treatment plan, a CT scan, the anatomical structures. For example, using an X-ray system and a twofold fusion, first on spine and posterior ribs (not moving with respiration) and then on sternum and anterior ribs (moving with respiration), it is made sure that the breath-hold during treatment is as close as possible to the breath hold during CT scanning.

Figure 5:
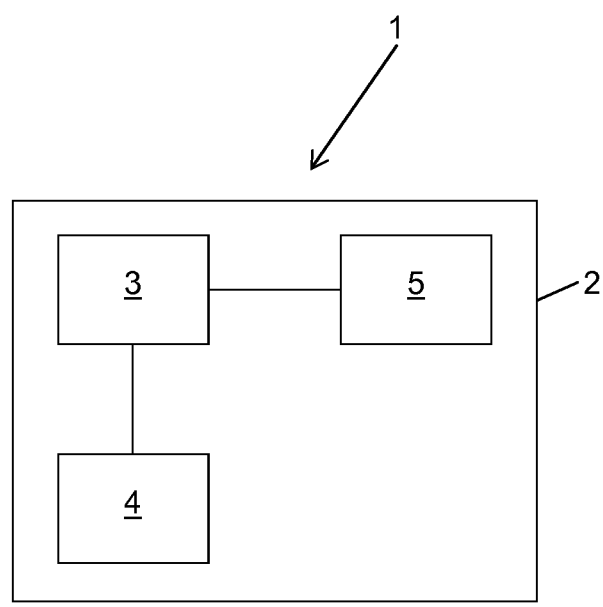
FIG. 5 shows a principle configuration of a system of a specific embodiment of the invention.

FIG. 5 shows a principle configuration of a system of a specific embodiment of the invention: the system 1 comprises a computing environment 2 including at least one computer 3 having at least one digital electronic processor which is operably coupled to at least one electronic data storage device 5 and an output device 4 (e.g. a graphical output device such as a display). The electronic data storage device 5 stores at least one of the medical image data or the electric stimulation device geometry data or the atlas data. The computer 3 is configured to output, to the output device 4, electronic signals representing a graphical representation of a result of the data processing conducted by the computer 3. Furthermore, the computing environment 2 can be coupled to other devices such as a patient positioning device, a patient treatment device, a medical imaging device or else.

The invention claimed is:

1. A computer-implemented medical data processing method for determining a difference in position of an imaged anatomical body part of a patient, the method comprising executing, on at least one processor of at least one computer, steps of:
acquiring, at the at least one processor, first patient image data describing a digital image of a first anatomical body part and a second anatomical body part during a first phase of inspiration and the position of the first anatomical body part and the position of the second anatomical body part during the first phase of inspiration in a first reference system associated with the first image data;
acquiring, at the at least one processor, second patient image data different from the first patient image data describing a digital image of the first anatomical body part during a second phase of inspiration and the position of the first anatomical body part during the second phase of inspiration in a second reference system;
acquiring, at the at least one processor, third patient image data different from the first patient image data and the second patient image data describing a digital image of the second anatomical body part during a third phase of inspiration and the position of the second anatomical body part during the third phase of inspiration in the second reference system;
determining, by the at least one processor, position transformation data describing a transformation between the first reference system and the second reference system, the position transformation data being determined based on the first patient image data and the third patient image data; and
determining, by the at least one processor and based on the first patient image data and the second patient image data and the position transformation data, position difference data describing a relative position between the position of the first anatomical body part during the first phase of inspiration and the position of the first anatomical body part during the second phase of inspiration,
wherein the first patient image data is three-dimensional image data, the second patient image data is two-dimensional image data, the first anatomical body part is a body part moving during inspiration, the second anatomical body part is a body part not moving during inspiration, the first phase of inspiration is a phase of deep inspiration breath hold at a first point in time, and the second phase of inspiration is a phase of deep inspiration breath hold at a second point in time, which is later than the first point in time.

2. The method of claim 1, wherein the method further comprises, before determining the position transformation data,
acquiring, at the at least one processor, atlas data describing a model of the second anatomical body part in a reference body,
wherein determining the position transformation data, by the at least one processor, is based on the first patient image data, the third patient image data and the atlas data.

3. The method according to claim 1, wherein the method further comprises the following step performed after determining the position transformation data:
determining, by the at least one processor and based on the position transformation data, control data describing a control command for controlling a patient support device to be moved according to the transformation.

4. The method according to claim 1, wherein the second patient image data describes a digital image of the first anatomical body part and the second anatomical body part during the second phase of inspiration and the position of the first anatomical body part and the position of the second anatomical body part during the second phase of inspiration in the second reference system and wherein the method comprises the following step performed after acquiring the second patient image data and before determining the position transformation data:
acquiring, at the at least one processor, atlas data describing a model of the second anatomical body part in a reference body,
wherein the position transformation data is determined, by the at least one processor, is based on the first patient image data and the second patient image data and the atlas data.

5. The method according to claim 1, wherein the method further comprises the following steps performed before acquiring the second patient image data:
acquiring, at the at least one processor, patient surface data describing the position of a surface of the patient in a third reference system associated with an optical position tracking system;
acquiring, at the at least one processor, surface offset data describing a value of an offset between the position of the patient surface described by the acquired patient surface data and a second position of the patient surface;
determining, by the at least one processor and based on the patient surface data and the surface offset data, corrected patient surface data describing the corrected position of the surface of the patient;
acquiring, at the at least one processor, the position transformation data;
acquiring, at the at least one processor, first camera position transformation data describing a transformation between the third reference system and the second reference system;
determining, by the at least one processor and based on the first camera position transformation data and the position transformation data, second camera position transformation data describing a transformation between the first reference system and the third reference system;
determining, by the at least one processor and based on the corrected patient surface data and the first patient image data and the second camera position transformation data, surface transformation data describing a transformation between the corrected position of the surface of the patient and an outer contour of the first patient image data.

6. The method of claim 5, further comprising after determining the surface transformation data and before acquiring the second patient image data,
determining, by the at least one processor and based on the surface transformation data, inspiration phase data describing a phase of inspiration of the patient,
wherein the patient surface data is acquired based on using an optical position tracking system by tracking a predetermined region of the surface of the patient which moves during inspiration, and wherein the optical position tracking system uses at least one of patterned light, infrared light, one or more optical markers or multiple cameras.

7. The method according to claim 6, wherein the method further comprises, after determining the inspiration phase data and before acquiring the second patient image data, determining, by the at least one processor and based on the inspiration phase data, control data describing a control signal for controlling a medical imaging device to acquire the second patient image data.

8. The method of claim 5, wherein the first patient image data further describes a digital image of a third anatomical body part during the first phase of inspiration and the position of the third anatomical body part during the first phase of inspiration in the first reference system and wherein the method comprises the following steps performed after acquiring the surface transformation data:

acquiring, at the at least one processor, planning data describing the position of the third anatomical body part in the first reference system;

determining, by the at least one processor and based on the corrected patient surface data and the surface transformation data and the planning data, target position data describing the relative position between the third anatomical body part and the corrected position of the surface of the patient.

9. The method according to claim 8, wherein the method further comprises the following steps performed after determining the position difference data:

acquiring, at the at least one processor, difference threshold data describing thresholds of the position difference data;

determining, by the at least one processor and based on the difference threshold data and the position difference data, first condition data describing whether the position difference data exceeds a first predetermined difference threshold;

if the first condition data describes that the position difference data exceeds the first predetermined difference threshold, determining, by the at least one processor and based on the position difference data, the surface offset data; and repeating the method starting at one of acquiring the patient surface data or acquiring the second patient image data.

10. The method of claim 9, further comprising, if the first condition data describes that the position difference data does not exceed the first predetermined difference threshold, continuing with a step of determining, by the at least one processor and based on the target position data and the corrected patient surface data and the inspiration phase data, treatment parameter data describing at least one treatment parameter of a treatment device.

11. The method of claim 9, further comprising determining, after acquiring the difference threshold data, by the at least one processor and based on the difference threshold data and the position difference data, second condition data describing whether the position difference data exceeds a second predetermined difference threshold; and if the second condition data describes that the position difference data exceeds the second predetermined difference threshold, determining, by the at least one processor and based on the position difference data, control data describing a control command for controlling a patient support device and/or a treatment device to be moved according to the position difference data.

12. The method of claim 11, further comprising, if the second condition data describes that the position difference data does not exceed the second predetermined difference threshold and if the first condition data describes that the position difference data does not exceed the first predetermined difference threshold, continuing with a step of determining, by the at least one processor and based on the target position data and the corrected patient surface data and the inspiration phase data, treatment parameter data describing at least one treatment parameter of a treatment device.

13. The method of claim 10, further comprising a step of outputting, by the at least one processor, the treatment parameter data to a treatment device, wherein the at least one treatment parameter describes deactivation of the treatment device in case at least one of the inspiration phase data indicates a predetermined inspiration phase not intended for treatment, or the patient surface data indicates a predetermined position of the surface of the patient not intended for treatment.

14. The method according to claim 10, wherein the method comprises the following step performed after determining the treatment parameter data:

repeating the method starting at one of acquiring the patient surface data or acquiring the second patient image data.

15. The method according to claim 1, wherein the third phase of inspiration is a phase of inspiration at a third point in time, which is later than the first point in time and earlier than the second point in time.

16. A non-transitory, computer-readable storage medium having stored thereon computer-executable instructions for a computer program which, when running on at least one processor of at least one computer or when loaded into a memory of at least one computer, causes the at least one computer to:

acquire first patient image data describing a digital image of a first anatomical body part and a second anatomical body part during a first phase of inspiration and the position of the first anatomical body part and the position of the second anatomical body part during the first phase of inspiration in a first reference system associated with the first image data;

acquire second patient image data different from the first patient image data describing a digital image of the first anatomical body part during a second phase of inspiration and the position of the first anatomical body part during the second phase of inspiration in a second reference system;

acquire third patient image data different from the first patient image data and the second patient image data describing a digital image of the second anatomical body part during a third phase of inspiration and the position of the second anatomical body part during the third phase of inspiration in the second reference system;

determine position transformation data describing a transformation between the first reference system and the second reference system, the position transformation data being determined based on the first patient image data and the third patient image data; and determine, based on the first patient image data and the second patient image data and the position transformation data, position difference data describing a relative position between the position of the first anatomical body part during the first phase of inspiration and the position of the first anatomical body part during the second phase of inspiration, wherein the first patient image data is three-dimensional image data, the second patient image data is two-dimensional image data, the first anatomical body part is a body part moving during inspiration, the second anatomical body part is a body part not moving during inspiration, the first phase of inspiration is a phase of deep inspiration breath hold at a first point in time, and the second phase of inspiration is a phase of deep inspiration breath hold at a second point in time, which is later than the first point in time.

17. A system for supporting determining a difference in position of an imaged anatomical body part of a patient, the system comprising:

a computer having computer-executable instructions that, when executed, configure the computer to:

acquire first patient image data describing a digital image of a first anatomical body part and a second anatomical body part during a first phase of inspiration and the position of the first anatomical body part and the position of the second anatomical body part during the first phase of inspiration in a first reference system associated with the first image data:

acquire second patient image data different from the first patient image data describing a digital image of the first anatomical body part during a second phase of inspiration and the position of the first anatomical body part during the second phase of inspiration in a second reference system;

acquire third patient image data different from the first patient image data and the second patient image data describing a digital image of the second anatomical body part during a third phase of inspiration and the position of the second anatomical body part during the third phase of inspiration in the second reference system;

determine position transformation data describing a transformation between the first reference system and the second reference system, the position transformation data being determined based on the first patient image data and the third patient image data; and determine, based on the first patient image data and the second patient image data and the position transformation data, position difference data describing a relative position between the position of the first anatomical body part during the first phase of inspiration and the position of the first anatomical body part during the second phase of inspiration; and a medical imaging device for acquiring patient image data, the medical imaging device being operably coupled to the computer for transmitting a signal to the computer corresponding to the patient image data, wherein the patient image data is at least one of the first patient image data, the second patient image data and third patient image data.

18. The system according to claim 17, further comprising an optical position tracking system for acquiring patient surface data describing the position of the surface of the patient, the optical position tracking system being operably coupled to the computer for transmitting a signal to the computer corresponding to the patient surface data.

19. The system according to claim 17, further comprising a treatment device operably coupled to the computer for receiving a signal from the computer corresponding to treatment parameter data describing at least one of activation or deactivation of a treatment device.

20. The system according to claim 17, further comprising a patient support device operably coupled to the computer for receiving a signal from the computer corresponding to control data describing a control command for controlling the patient support device to be moved.

* * * * *